United States Patent [19]

Wright

[11] 4,071,316

[45] * Jan. 31, 1978

[54] SILICONE COMPOSITION FOR ANALYZING BLOOD SAMPLES

[75] Inventor: John H. Wright, Elnora, N.Y.

[73] Assignee: General Electric Company, Waterford, N.Y.

[*] Notice: The portion of the term of this patent subsequent to Apr. 19, 1994, has been disclaimed.

[21] Appl. No.: 752,057

[22] Filed: Dec. 20, 1976

Related U.S. Application Data

[63] Continuation-in-part of Ser. No. 634,563, Nov. 24, 1975, Pat. No. 4,018,564.

[51] Int. Cl.$^2$ ............................ C07F 7/18; G01N 33/16
[52] U.S. Cl. ............................ 23/230 B; 106/287 SB; 210/DIG. 23; 252/36; 260/448.2 R
[58] Field of Search ............. 23/230 B; 210/DIG. 23

[56] References Cited

U.S. PATENT DOCUMENTS

| | | | |
|---|---|---|---|
| 3,669,884 | 6/1972 | Wright | 252/36 |
| 3,780,935 | 12/1973 | Lukacs | 210/DIG. 23 |
| 3,852,194 | 12/1974 | Zine | 210/DIG. 23 |
| 3,920,549 | 11/1975 | Gigliello | 210/DIG. 23 |
| 4,018,564 | 4/1977 | Wright | 23/230 B |

*Primary Examiner*—Sidney Marantz
*Attorney, Agent, or Firm*—E. Philip Koltos; John L. Young; Frank L. Neuhauser

[57] ABSTRACT

A silicone composition with controlled rheological properties and a controlled specific gravity that may vary from 1.035 to 1.06 comprising a diorganopolysiloxane and blends of diorganopolysiloxanes which are compatible with each other which polysiloxanes have a viscosity that may vary anywhere from 10,000 to 500,000 centipoise at 25° C, and a filler selected from the class consisting of fumed silica, precipitated silica, fumed silica treated with a silicone compound, precipitated silica treated with a silicone compound. Such compositions may be utilized with blood samples when the blood sample is treated to separate the blood clots from the blood serum which composition forms an integral barrier between such separated blood clots and the blood serum.

14 Claims, No Drawings

SILICONE COMPOSITION FOR ANALYZING BLOOD SAMPLES

BACKGROUND OF THE INVENTION

This application is a continuation-in-part of Ser. No. 634,563, filed on Nov. 24, 1975, now U.S. Pat. No. 4,018,564.

The present invention relates to a silicone composition with controlled rheological properties and a specific gravity that varies anywhere from 1.035 to 1.06 and more particularly the present invention relates to silicone compositions with controlled rheological properties and a specific gravity that varies from 1.035 to 1.06 which composition may be utilized in blood serum separation techniques.

Silicone compositions comprising a diorganopolysiloxane fluid and silica filler are well known. For instance, see U.S. Pat. Nos. of John H. Wright — 3,037,933, 3,103,491, 3,145,175, 3,197,319, 3,197,728, 3,304,259, 3,453,210, 3,537,997, 3,671,429, 3,664,953, 3,669,884, 3,473,089, 3,882,033, 3,885,984 and 3,915,924. The silica filler is incorporated into the diorganopolysiloxane fluid as a thickening agent to produce a silicone grease or a channel sealant. Various additives are added to such compositions for one purpose or another. However, the full extent of the properties and uses of such compositions and specifically the full extent of specific compositions within the broad disclosures of the above patents was not appreciated.

Recently, it has become highly desirable to produce a silicone composition with controlled rheological properties and a controlled specific gravity which will allow materials with a higher specific gravity than the silicone composition to pass therethrough and separate from compositions with a lighter specific gravity than the silicone composition. It is desired that such silicone compositions form an integral layer separating the low specific gravity material from the high specific gravity material. Such composition would strongly facilitate the separation of low specific gravity from high specific gravity material.

One of the reasons why a silicone composition was envisioned for such a particular use was because many silicones are basically inert to other reactive materials and also tend to be non-toxic. Accordingly, such a silicone composition has been desired for a clean and efficient separation of a high specific gravity fluid from a low specific gravity fluid. One particular specific application where such a silicone composition was desired was in the analysis of human and animal blood samples. Normally, such blood samples are taken and there may be added to them a catalytic ingredient which will coagulate in the blood sample the undesirable material from the blood serum which is to be utilized for medical analysis. The undesirable material will then be allowed to settle and separate out from the blood serum. However, this procedure left something to be desired in that some of the undesirable blood clotting material was usually present or found in the blood serum that was poured out, irrespective of how careful the separation procedure was carried out.

Accordingly, it was highly desirable to add some type of composition to the blood sample so as to permit a clean and efficient separation of the blood clot material from the blood serum. It was desired that such a composition would allow the blood clot and higher specific gravity material to flow through the composition and settle at the bottom of the sample vessel, and when agitation was terminated that such composition would form an integral layer completely separating the blood serum from the blood clots whereupon the blood serum could be poured off in essentially a pure form free of undesirable materials so that such blood serum could be utilized in medical laboratory analysis. It was also highly desirable that such a composition for separating blood clots from the blood serum does not give off any of its ingredients into the blood serum since such ingredients might deleteriously affect the subsequent medical laboratory analysis.

Accordingly, as stated previously, while various materials were tried for this purpose and specifically ones that had a specific gravity intermediate between the specific gravity of the blood clot and the specific gravity of the blood serum, no composition has hereto been found which has the proper combination of rheological properties and specific gravity properties.

Accordingly, it is one object of the present invention to provide for a silicone composition that has controlled rheological properties and a specific gravity that varies from 1.035 to 1.06.

It is another object of the present invention to provide for a silicone composition with controlled rheological properties and specific gravity that varies from 1.035 to 1.06 which composition is basically inert and nontoxic.

It is an additional object of the present invention to provide for a silicone composition with controlled rheological properties and specific gravity that varies from 1.035 to 1.06 which has very little bleed out of its ingredients under intensive agitation conditions.

It is still another object of the present invention to provide for a silicone composition with controlled rheological properties and specific gravity that varies from 1.035 to 1.06 which is suitable in the separation of blood serum from blood clots in medical laboratory analysis.

SUMMARY OF THE INVENTION

In accordance with the above objects there is provided by the present invention a silicone composition with controlled rheological properties and a specific gravity that varies from 1.035 to 1.06 comprising (A) 100 parts by weight of a diorganopolysiloxane and blends of such polysiloxanes which are compatible with each other where such a diorganopolysiloxane polymer has a viscosity varying from 10,000 to 500,000 centipoise at 25° C where the organo groups are selected from the class consisting of monovalent hydrocarbon radicals and halogenated monovalent hydrocarbon radicals and (B) from 3 to 50 parts by weight of a filler selected from the class consisting of fumed silica, precipitated silica, fumed silica treated with a silicone compound, precipitated silica treated with a silicone compound where the amount of treated fumed and treated precipitated silica varies from 2 to 98% by weight of the total silica present.

The above discloses a more preferred silicone composition in which certain silica fillers must be present for a silicone composition with the desired controlled rheological properties discussed above. For any use whatsover the above ranges of silica filler must contain both treated and untreated silica fillers as specified, which filler can be either precipitated silica or fumed silica. For blood analysis, precipitated silica is undesirable since it contains contaminates.

Accordingly, for a blood analysis composition only fumed silica is desired in the silicone composition. Yet for such blood analysis it has been found that a broader range of treated to untreated fumed silica can be utilized, that is, the preferred of 2 to 98% of treated filler versus untreated filler may be utilized for blood analysis, but there also may be utilized for such a blood analysis a completely untreated fumed silica or completely treated fumed silica. Preferably from 2 to 98% by weight and more specifically, 25 to 75% by weight of treated fumed silica based on the total fumed silica present is utilized in the present composition when it is used for blood analysis.

There is also provided by the present invention a method for separating the blood serum in a blood sample composed of blood serum and blood clots in part comprising (1) adding to the blood sample a small but effective amount of a blood separating composition having controlled rheological properties and a specific gravity that varies from 1.035 to 1.06 wherein said composition comprises (A) 100 parts by weight of a diorganopolysiloxane and blends of such diorganopolysiloxanes which are compatible with each other of a viscosity varying from 10,000 to 500,000 centipoise at 25° C, where the organo groups are selected from the class consisting of monovalent hydrocarbon radicals and halogenated monovalent hydrocarbon radicals, and (B) from 3 to 25 parts by weight of a filler selected from the class consisting of fumed silica and fumed silica treated with a silicone compound wherein the amount of treated fumed silica may vary from 0 to 100% by weight of the total silica present, and preferably varies from 2 to 98% by weight of the total silica present and more preferably varies from 25 to 75% by weight of the total silica present.

It should be mentioned at this time that by the compatibility of the diorganopolysiloxanes that are to be used in the present composition it is meant that with the different types of substituted diorganopolysiloxanes that are used in a particular blend that such diorganopolysiloxanes when mixed together will not separate out. The compatibility of such diorganopolysiloxane fluids is well known to a silicone chemist skilled in the art.

In addition, as has been pointed out, irrespective of whether a blend of diorganopolysiloxanes or a single polymer specie is utilized to form the present composition, the final viscosity of such composition must be within the range of 10,000 to 500,000 centipoise at 25° C.

DESCRIPTION OF THE PREFERRED EMBODIMENT

The organo groups in the diorganopolysiloxanes in the present composition are selected from any monovalent hydrocarbon radicals and halogenated monovalent hydrocarbon radicals. Exemplary of such monovalent hydrocarbon radicals and halogenated monovalent hydrocarbon radicals are alkyl radicals such as, methyl, ethyl, propyl and etc.; alkenyl radicals such as, vinyl, allyl and etc.; cycloalkyl radicals such as, cyclohexyl, cycloheptyl and etc.; monovalent aromatic radicals such as, phenyl, methylphenyl and etc.; halogenated monovalent aromatic radicals such as, chlorophenyl and etc.; and halogenated alkyl radicals such as, trifluoropropyl. Most preferably, the organo radicals of such diorganopolysiloxane polymers are selected from alkyl radicals of 1 to 8 carbon atoms such as, methyl, and from phenyl, chlorophenyl, tetrachlorophenyl, and trifluoropropyl radicals. Such diorganopolysiloxanes do not have to be substituted homogeneously with a particular type of hydrocarbon radical or halogenated hydrocarbon radical, they may be substituted with any mixture of the above radicals.

As indicated above one of the preferred diorganopolysiloxanes that may be utilized in the instant invention to form a blood separating composition comprises a polysiloxane that is prepared by the hydrolysis and condensation product of chlorophenyl chlorosilanes and methylchlorosilanes in the presence from 1 to 10% of tin chloride wherein the mixture is heated at at a temperature of from 460° F to 750° F from 1 to 6 hours to allow the ingredients to react. After the reaction is completed the residue diorganopolysiloxane is obtained by simply vacuum stripping the reaction product at temperatures above 600° F to remove the by-products and unreacted chlorosilanes. Accordingly, there is obtained a diorganopolysiloxane polymer where in the substituting groups are a mixture of methyl and chlorophenyls. Although such methyl, chlorophenyl substituted polysiloxane polymers are advantageously utilized in the instant case, in a more preferred embodiment, there is desirably utilized a diorganopolysiloxane polymer wherein the organo groups are selected from a mixture of methyl and tetrachlorophenyl. Such a polysiloxane polymer is obtained by reacting at a temperature of from 460° F to 750° F from 1 to 6 hours a mixture of from about 5 to 25 parts of tetrachlorophenyltrichlorosilanes 55 to 92 parts by weight of dimethyldichlorosilane and 3 to 20 parts by weight of trimethylchlorosilane in the presence of from 1 to 10% of tin chloride based on the weight of the reactants. The unreacted chlorosilanes, as well as the by-products as stripped off from the polysiloxane product by stripping under vacuum at temperatures of about 600° F. By this procedure there is obtained a diorganopolysiloxane polymer where the organo groups are a mixture of methyl and tetrachlorophenyl where the diorganopolysiloxane polymer has at a weight concentration of about 5 to 25 parts of tetrachlorophenyl substituting groups. All the parts and percentages given above are by weight. The preferred methyl, tetrachlorophenyl substituted polysiloxane polymers are utilized advantageously in the instant case as the basic polysiloxane polymer to produce one of the preferred blood separating compositions within the scope of the instant invention. Accordingly although the methyl chlorophenyl substituted polysiloxane polymer may be utilized to form the basic polysiloxane in the blood separating compositions of the instant case a more preferred polysiloxane polymer which may be utilized is one having methyl and tetrachlorophenyl substituting groups. The methyl, tetrachlorophenyl substituted polysiloxanes which form a blood separating composition within the scope of the instant case have the advantage that the resulting blood separating composition which is formed in accordance with the instant case has desirable flow properties. The preparation of such methyl chlorophenyl substituted polysiloxanes and methyl and tetrachlorophenyl substituted polysiloxanes is set forth in Brown U.S. Pat. No. 2,970,162 which is incorporated into the present case by reference. As such it will not be necessary to discuss further the preparation and availability of such polysiloxanes. It should also be noted that such chlorinated phenyl and methyl substituted polysiloxanes may be utilized in a blend with other polysiloxanes as was discussed above as long as the polysiloxanes are compatible with each other. Blends containing such chlorinated phenyl and tetrachlorophenyl substituted polysiloxanes can be utilized as the basic fluids in forming the blood separating compositions of the instant case.

The only precaution that has to be exercised is when a blend of such diorganopolysiloxanes is utilized that the type of substitution utilized in the particular polymer species be such that the different diorganopolysiloxane polymer species be compatible with each other, that is to say that such polymer species do not separate from each other upon mixing. Although a single polymer species of a diorganopolysiloxane may be utilized in the composition of the present invention, any blend of two or more of such polymer species with the same or different substitutions may be utilized to form the basic diorganopolysiloxane ingredient in the composition of the present invention.

It is necessary in the present invention that such individual polymer species of diorganopolysiloxanes utilized in the composition of the present invention or blends of such diorganopolysiloxanes have a final viscosity that varies from 10,000 to 500,000 centipoise at 25° C if the final composition is to have the desired rheological properties.

With this in mind, it can be envisioned that in the base polymer ingredient of the present composition there may be used diorganopolysiloxanes of a viscosity that varies anywhere from 50 centipoise at 25° C to 500,000 centipoise at 25° C. If low viscosity diorganopolysiloxanes are utilized and that is one specifically with a viscosity below 10,000 centipoise at 25° C or even above that range, there may be blended into such diorganopolysiloxanes high viscosity diorganopolysiloxanes having a viscosity in excess of 600,000 centipoise and up to 200,000,000 centipoise at 25° C. This blending may be accomplished of such high viscosity diorganopolysiloxanes with low viscosity diorganopolysiloxanes so long as the two different types of polysiloxanes are compatible with each other and so long as the final end viscosity of the blend of polysiloxanes is within the range of 10,000 to 500,000 centipoise at 25° C. Most preferably, when such high viscosity diorganopolysiloxanes are utilized it is preferred to utilize in terms of the total concentration of diorganopolysiloxanes 1 to 25 parts of the high viscosity diorganopolysiloxanes with a viscosity in excess of 600,000 centipoise at 25° C with 1 to 75 parts of the low viscosity diorganopolysiloxanes of a viscosity of anywhere from 50 to 500,000 centipoise at 25° C.

As can be appreciated, the only properties in the utilization of such blends of diorganopolysiloxanes is that the final blended polymer composition have a viscosity within the range of 10,000 to 500,000 centipoise at 25° C and that the individual polymer species of diorganopolysiloxanes be compatible with each other, that is, they do not separate upon mixing. Such compatibility of different diorganopolysiloxane polymers is well within the knowledge of the skilled silicone chemists.

To this basic diorganopolysiloxane polymer or blends of polymers there must be added a certain amount of silica filler selected from fumed silica and precipitated silica. In the more preferred embodiment of the present invention 2 to 98% by weight and more preferably 25 to 75% by weight of the silica filler must be treated with a silicone compound. However, it should be noted while such precipitated silica can be utilized in the present composition when the present composition is utilized in separation techniques for fluids other than blood, such precipitated silica cannot be used in the present composition when it is to be used for blood analysis. The reason for this is that precipitated silica has undesirable impurities in it due to the process by which it is produced which impurities may affect the subsequent analysis of the blood serum. Accordingly, for purposes of blood analysis it has been found that only fumed silica, whether treated or untreated, can be utilized in the present composition since fumed silica has a high purity.

It should also be noted that with respect to blood analysis the present composition can be utilized effectively even when there is essentially all untreated fumed silica filler in the present composition or even when there is all treated fumed silica filler in the present composition. However, the more preferred form of the fumed silica that is utilized in the present composition even for blood analysis is the case where the amount of treated fumed silica filler varies from 2 to 98% by weight of the total silica present and more preferably varies from 25 to 75% by weight of the total silica filler present.

The treatment of such silica fillers whether fumed silica or precipitated silica with a silicone compound is well known in the art. For instance, treatment of silica fillers with cyclicpolysiloxane is disclosed in the Lucas, U.S. Pat. No. 2,938,009, which is hereby incorporated by reference, while the treatment of silica fillers with cyclicpolysiloxanes as well as with silazanes are disclosed in the patent of Alfred H. Smith, U.S. Pat. No. 3,635,743 and Melvin D. Beers, U.S. Pat. No. 3,847,848, which patents are also hereby incorporated into the present case by reference.

Preferred treating agents for the silica fillers whether precipitated or fumed silica are octamethylcyclictetrasiloxane or hexamethyldisilazane. The fillers may be treated with the silicone compounds individually in accordance with the disclosures of the foregoing patents or consecutively as may be desired.

It should be mentioned in terms of explanation that the untreated filler lends consistency to the silicone composition of the present invention. The advantage of having the treated filler in the composition of the present invention is that it improves it rheological properties, that is, the properties of the instant composition in its ability to flow or allow higher specific gravity materials to pass through the composition and at the same time flow back to its initial state after agitation of the composition.

Accordingly, although for blood analysis purpose the instant composition can have purely untreated fumed silica, such composition suffers in that it does not have as desirable rheological properties as would be desired. In addition, even though completely treated filler can be used in the instant composition for blood analysis, the composition does not have as high a consistency as would be desired without unduly increasing the filler loading and resulting in a composition with a specific gravity beyond the desired range.

It is desired that per 100 parts of the diorganopolysiloxane polymer specie blends or polymer species, as specified above, that there be utilized from 3 to 50 parts of total silica filler, whether treated or untreated. If less than 3 parts of silica filler is utilized in the instant composition, then the composition will not have a sufficient consistency even when the silica filler is completely untreated. If more than 50 parts by weight of a silica filler is utilized in the instant composition then the composition may suffer from several disadvantages, including poor rheological properties and a composition that does not have the required specific gravity. More preferably, there is utilized from 4 to 18 parts by weight of total silica of whatever type within the limitations specified above, per 100 parts by weight of the diorganopolysiloxane polymer species or blends of polymers.

The third ingredient that is necessary in the instant composition, which is an optional but desirable ingredient, is a stabilizing compound. The necessity for having such a compound in the instant composition is that the instant composition in its broadest form upon use will tend to bleed out some of the diorganopolysiloxane polymer from the composition which diorganopolysiloxane polymer may undesirably contaminate the fluid that is being separated such as, for instance, blood serum.

Accordingly, it is highly desirable to have a stabilizing compound in the instant composition to prevent or minimize as mush as possible the bleed out of any of the diorganopolysiloxane polymer species when a single polymer specie composition is used or when a blend of diorgano polymer species is utilized in the instant composition.

Accordingly, one preferred such stabilizing compound is a polyether. Generally, there may be utilized from 0.05 to 3 parts by weight per 100 parts of the diorganopolysiloxanes of a stabilizing compound of the formula,

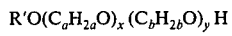

$$R'O(C_aH_{2a}O)_x(C_bH_{2b}O)_yH$$

where R' is a monovalent hydrocarbon radical and is preferably selected from the class of hydrogen and lower alkyl radicals having from 1 to 7 carbon atoms, $a$ and $b$ are integers equal to from 1 to 4, inclusive, $x$ is an integer equal to from about 4 to 50 or more and $y$ is a whole number equal to from 0 to 50. Such polyethers are well known compounds and are sold by various tradenames and various molecular configurations by many chemical companies such as, for instance, Union Carbide Corporation, New York, N.Y. If lower concentrations than the above of the polyethers are utilized in the instant composition, then the instant composition will not be sufficiently stabilized. If more than 3 parts are utilized and this may be done, such additional amounts of stabilizing compounds do not serve any additional stabilizing affects in the instant composition. More preferably, there is utilized in the instant composition from 0.01 to 2 parts by weight of the above polyether stabilizing compound, per 100 parts of the diorganopolysiloxanes utilized in the instant composition. In a preferred form, the instant composition may be utilized in blood analysis and more specifically in a blood separation technique, that is, separating blood clots and other undesirable matter from the blood serum which is to be subjected to medical analysis. In such blood separation techniques, the present silicone composition is utilized in an amount that is small but effective to function as a separating agent between the blood serum and the blood clots. More preferably, the instant composition for blood analysis is utilized at a concentration of 1% to 75% by weight of the total composition, that is, including the weight of the blood sample and the instant composition and more preferably at a concentration of 5 to 25% by weight of such total composition.

Accordingly, after the blood sample has been added to a glass vessel in which the blood clots precipitates as well as other undesirable matter, the mixture of the instant composition which has previously been added and the blood sample is then desirably put in a centrifuge whereupon the blood clots and the undesirable matter settle to the bottom of the vessel leaving the blood serum at the top of the vessel with the instant composition forming a separation layer between the blood serum and the undesirable blood matter.

In the above description of the instant invention, other ingredients may be added to the instant composition as may be desired for a particular use of the composition. All parts in the instant case are by weight.

The examples below are given for the purpose of more clearly defining the instant invention but are not intended in any way or manner to limit the definition of the instant invention.

EXAMPLE 1

To 86 parts of a dimethylpolysiloxane of 10,000 centipoise viscosity at 25° C there is mixed 12 parts of a hexamethyldisilazane, treated fumed silica and one part of untreated fumed silica. To this composition there is added one percent by weight of Ucon LB-1145, tradename for a polyether sold by the Union Carbide Corporation, and the resulting composition is then milled for two passes on a three-roll paint mill to completely mix the composition. The resulting composition had a penetration of 346, a specific gravity of 1.042 and an oil separation of less than 1 percent under 240,000 forces of gravity for 6 hours. The above composition performed well as a blood separation compound.

Another silicone composition was prepared in which as the base polysiloxane there was used dimethylpolysiloxane by itself of 100 centipoise viscosity to which were added the same amount and types of other ingredients as were added in the above composition and in which the mixing was carried out in the same manner as indicated above to produce a composition that had a penetration of 340, a specific gravity of 1.0415, but which when tested had a 20% separation of the fluid from the filler under 240,000 forces of gravity for 6 hours, indicating that such a composition was highly undesirable for blood separation techniques.

EXAMPLE 2

A composition was prepared using a methylphenylpolysiloxane polymer in which there was sufficient phenyl in the polymer to give the fluid a specific gravity of 1.02 and wherein the fluid had a viscosity of 10,000 centipoise at 25° C. This fluid was mixed with 4 parts of a finely divided silica and one part of a polyether, Pluracol V-7, manufactured and sold by Wyandotte Chemical Co. The resulting ingredients were then taken and mixed and milled on a three-roll paint mill with two passes in the mill. The resulting composition when tested had a penetration of 330, a specific gravity of 1.0425 and an oil separation under 240,000 forces of gravity for 6 hours of 2%. This composition exhibited flow properties under low forces as well as proper sealing effects in blood separation, and was found to be a proper composition for a blood separation.

EXAMPLE 3

A composition was made by taking 8.5 parts of a fluid consisting of 78 parts of a methylchlorophenyl-substituted polysiloxane and 22 parts of a dimethylpolysiloxane of a viscosity of 15,000,000 centipoise at 25° C. To this there was added 4 parts of a finely divided fumed silica which was not treated and one part of a polyether, Igepal RC-520, manufactured and sold by the Antarn Chemical Co.. This composition when tested had a penetration of 353, a specific gravity of 1.0415 and an oil separation under 240,000 forces of gravity for 6 hours of 0.075% and rheological properties which permitted it to stay where placed with no flow and to flow under low pressures.

EXAMPLE 4

A composition was prepared similar to Example 1, in the quantities of the basic ingredients indicated in Example 1, except for the diorganopolysiloxane ingredients where there was utilized 75% by weight of the total diorganopolysiloxanes of a dimethylpolysiloxane of 50 centipoise at 25° C and 25% by weight of a dimethylpolysiloxane gum of 50,000,000 centipoise at 25° C. The other ingredients and quantities of other ingredients that were added to the blend of polymers were the same as in Example 1. The composition when mixed in the manner of Example 1 had a penetration of 355, a specific gravity of 1.040, an oil separation of 240,000 forces of gravity for 6 hours at 0.9%. This composition had excellent blood separating characteristics.

EXAMPLE 5

There was prepared a composition composed of 4 parts of a methylchlorophenyl substituted organopolysiloxane of 50 centipoise viscosity at 25° C, and 6 parts of a dimethylpolysiloxane fluid of 500,000 centipoise at 25° C. To this total amount taken as 88.5 parts there was mixed with it 8 parts of a hexamethyldisilazane treated fumed silica, 2.5 parts of untreated fumed silica and 1% by weight of the polyether specified in Example 1.

The mixture was milled twice on the three-roll paint mill to give a compound with a penetration of 348, a specific gravity of 1.0413, an oil separation at 240,000 forces of gravity for 6 hours of 0.85% and which composition exhibited excellent rheological flow and separation properties in blood separation.

EXAMPLE 6

There is prepared a composition composed of 4 parts by weight methyl tetrachlorophenyl substituted polysiloxane of 60 centipoise viscosity at 25° C and 6 parts of dimethylpolysiloxane fluid of 500,000 centipoise at 25° C. This total mixture which has an end viscosity of 20,000 centipoise at 25° C and which total mixture is taken as 88.5 parts by weight, there is mixed with into it 8 parts octymethylcyclitetrasiloxane treated fumed silica 2.5 parts of untreated fumed silica and 1% by weight of the polyether specified in Example 1. The mixture is then milled twice on a three-roll paint mill to give a compound with a penetration of 352, a specific gravity of 1.0416, an oil separation of 240,000 forces of gravity for 6 hours of 0.85%. This composition exhibits excellent rheological flow and separation properties in blood separation.

It should be mentioned that a necessary part of the properties of the instant composition is its end specific gravity which must be in the range of 1.035 to 1.06 and specifically so for blood separation. Although variations may be made in specific gravity by the type of diorganopolysiloxanes and blends of such polysiloxanes that are used with the amount of filler, nevertheless, what has been accomplished by the instant invention is a proper combination of the above specific gravity properties with the desired rheological properties. In addition, the final instant composition may be prepared by mixing the ingredients in any way or manner with no special precautions except for keeping the ingredients pure and the final composition as pure as possible. Preferably, the ingredients are mixed on a mill.

It should also be noted as specified previously that the basic ingredients of the present composition are basically inert and non-toxic thus making the present composition suitable for many applications.

I claim:

1. A blood analysis composition comprising a small but effective amount of blood necessary for laboratory analysis and a small but effective amount of blood-separating composition having controlled rheological properties and a specific gravity that varies from 1.035 to 1.06 wherein said composition comprises (a) 100 by weight of a blend of diorganopolysiloxanes which are compatible with each other of a viscosity varying from 10,000 to 500,000 centipoise at 25° C, where the organo groups are methyl and a mixture of methyl and tetrachlorophenyl; (b) from 3 to 50 parts by weight of a filler selected from the group consisting of fumed silica and fumed silica treated with a silicone compound wherein the amount of treated fumed silica varies from 0 to 100% by weight of the total silica present; and (c) from 0.05 to 3 parts by weight of a stabilizing compound of the formula,

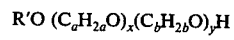

$$R'O\,(C_aH_{2a}O)_x(C_bH_{2b}O)_yH$$

wherein R' is a member selected from the group consisting of hydrogen and lower alkyl radicals having from 1 to 7 carbon atoms, $a$ and $b$ are integers equal to from 1 to 4 inclusive, $x$ is an integer equal to from 4 to 50 or more, and $y$ is a whole number equal to from 0 to 50.

2. The blood analysis composition of claim 1 wherein the amount of the blood-separating composition varies from 1 to 75% by weight of the total composition.

3. The blood analysis composition of claim 1 wherein the blood-separating composition in said blends of said diorganopolysiloxane there is present from 1 to 25 parts of a diorganopolysiloxane of a viscosity varying from 600,000 centipoise to 200,000,000 centipoise at 25° C, and in said blends of diorganopolysiloxane there is present from 1 to 75 parts of diorganopolysiloxane of a viscosity varying from 50 to 500,000 centipoise at 25° C, which diorganopolysiloxanes must be compatible with each other and such that the viscosity of the final blend must very from 10,000 to 500,000 centipoise at 25° C.

4. The blood analysis composition of claim 1 wherein in the blood-separating composition the silicone compound used to treat the silica is selected from the group consisting of cyclicpolysiloxanes and silazanes.

5. The blood analysis composition of claim 1 wherein in the blood-separating composition the amount of treated fumed silica in the total amount of silica present varies from 25 to 75% by weight.

6. The blood analysis composition of claim 1 wherein in the blood-separating composition the total amount of silica varies from 4 to 18 parts.

7. The blood analysis composition of claim 1 wherein in the blood-separating composition the stabilizing compound is present at a concentration of 0.1 to 2 parts by weight.

8. A method for analyzing a blood sample composed of blood serum and blood clots in part comprising adding to said blood sample a small but effective amount of blood-separating composition having controlled rheological properties and a specific gravity that varies from 1.035 to 1.06 wherein said composition comprises (a) 100 parts by weight of a blend of diorganopolysiloxanes which are compatible with each other of a viscosity varying from 10,000 to 500,000 centipoise at 24° C where the organo groups are methyl and a mixture of methyl and tetrachlorophenyl; (b) from 3 to 50 parts by weight of a filler selected from the group consisting of a fumed silica and fumed silica treated with a silicone compound wherein the amount of treated fumed silica varies from 0 to 100% by weight of the total silica present; and (c) from 0.05 to 3 parts by weight of a stabilizing compound of the formula,

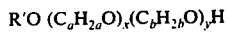

wherein R' is a member selected from the group consisting of hydrogen and lower alkyl radicals having from 1 to 7 carbon atoms, $a$ and $b$ are integers equal to from 1 to 4 inclusive, $x$ is an integer equal to from about 4 to 5 or more and $y$ is a whole number equal to from 0 to 50; and centrifuging the blood sample and said blood-separating composition to separate said blood serum from said blood clost with said blood-separating composition forming an integral barrier between said blood clots and said blood serum.

9. The method of claim 8 wherein the amount of said blood-separating composition varies from 1 to 75% by weight of the total composition.

10. The method of claim 8 wherein in said blood-separating composition in said blends of said diorganopolysiloxane there is present from 1 to 25 parts of a diorganopolysiloxane of a viscosity varying from 600,000 to 200,000,000 centipoise at 25° C and in said blends of diorganopolysiloxanes there is present from 1 to 75 parts of diorganopolysiloxanes of a viscosity varying from 50 to 500,000 centipoise at 25° C which diorganopolysiloxanes must be compatible with each other and such that the viscosity of the final blend must vary from 10,000 to 500,000 centipoise at 25° C.

11. The method of claim 8 wherein in said blood-separating composition the silicone compound used to treat the silica is selected from the group consisting of cyclicpolysiloxanes and silazanes.

12. The method of claim 8 wherein in the blood-separating composition the amount of the treated fumed silica in the total amount of silica varies from 25 to 75% by weight.

13. The method of claim 8 wherein in said blood-separating composition the total amount of silica varies from 4 to 18 parts.

14. The method of claim 8 wherein in said blood-separating composition the stabilizing compound is present at a concentration of 0.1 to 2 parts by weight.